(12) United States Patent
Vacek

(10) Patent No.: US 7,392,717 B1
(45) Date of Patent: *Jul. 1, 2008

(54) TESTING APPARATUS AND METHOD FOR COMPOSITE ARTICLES

(75) Inventor: Matthew Vacek, Brownsville, MN (US)

(73) Assignee: Miken Sports, LLC, Caledonia, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/833,231

(22) Filed: Aug. 3, 2007

Related U.S. Application Data

(63) Continuation of application No. 11/198,956, filed on Aug. 8, 2005, now Pat. No. 7,334,488, which is a continuation of application No. 10/952,483, filed on Sep. 28, 2004, now Pat. No. 7,017,427, which is a continuation of application No. 10/842,833, filed on May 11, 2004, now abandoned.

(60) Provisional application No. 60/470,540, filed on May 14, 2003.

(51) Int. Cl.
G01L 1/04 (2006.01)
G01L 1/22 (2006.01)

(52) U.S. Cl. ................................. 73/862.631
(58) Field of Classification Search ............. 73/862.631
See application file for complete search history.

(56) References Cited

U.S. PATENT DOCUMENTS

| | | | |
|---|---|---|---|
| 3,987,669 A | 10/1976 | Daneshy | |
| 4,198,870 A | 4/1980 | Barker | |
| 4,343,467 A * | 8/1982 | Newcomb et al. | 473/567 |
| 4,856,335 A | 8/1989 | Tornberg | |
| 4,892,303 A | 1/1990 | Lohre | |
| 5,024,436 A | 6/1991 | Vento | |
| 5,031,909 A | 7/1991 | Pecker | |
| 5,255,562 A | 10/1993 | Yamamoto et al. | |
| 5,303,917 A | 4/1994 | Uke | |
| 5,757,266 A * | 5/1998 | Rider et al. | 340/323 R |
| 5,857,694 A | 1/1999 | Lazarus et al. | |
| 5,907,211 A | 5/1999 | Hall et al. | |
| 5,951,410 A * | 9/1999 | Butler et al. | 473/223 |
| 6,334,824 B1 | 1/2002 | Filice et al. | |
| 6,432,007 B1 * | 8/2002 | Filice et al. | 473/566 |
| 6,508,731 B1 | 1/2003 | Feeney et al. | |
| 6,663,517 B2 | 12/2003 | Buiatti et al. | |
| 6,716,034 B2 | 4/2004 | Casanova, Jr. et al. | |
| 6,743,127 B2 * | 6/2004 | Eggiman et al. | 473/567 |
| 7,017,427 B1 * | 3/2006 | Vacek | 73/862.631 |
| 7,097,578 B2 | 8/2006 | Guenther et al. | |
| 7,175,552 B2 | 2/2007 | Fritzke et al. | |
| 2004/0209716 A1 | 10/2004 | Vacek et al. | |

* cited by examiner

*Primary Examiner*—Edward Lefkowitz
*Assistant Examiner*—Octavia Davis
(74) *Attorney, Agent, or Firm*—Waddey & Patterson, P.C.; Phillip E. Walker

(57) ABSTRACT

A testing apparatus for a composite material includes a base for holding the composite article, a load cell for placing a selected load on a portion of the composite article, and a displacement measuring device for measuring the amount of displacement for a selected load. In operation, a composite article is placed in a testing apparatus, a selected load is placed on the composite article, and the displacement of the composite article is measured.

18 Claims, 4 Drawing Sheets

TESTING APPARATUS AND METHOD FOR COMPOSITE ARTICLES

CROSS-REFERENCE TO RELATED APPLICATIONS

This application is a continuation of U.S. application Ser. No. 11/198,956 filed Aug. 2, 2005 which is a continuation of U.S. application Ser. No. 10/952,483 filed Sep. 28, 2004, now U.S. Pat. No. 7,017,427 as issued on Mar. 28, 2006, which is a continuation of U.S. application Ser. No. 10/842,833 filed May 11, 2004, now abandoned, which claims priority to Application Ser. No. 60/470,540 filed May 14, 2003, of which all applications are incorporated herein by reference.

FIELD OF THE INVENTION

The present invention relates to the field of testing and more particularly to a testing apparatus and method for composite articles.

BACKGROUND OF THE INVENTION

For several decades now, products have been made of composite materials. In the early days, many articles were made of fiberglass. Boat hulls were made of fiberglass. Wooden hulled boats were also covered by fiberglass to reduce or eliminate leaks and to lengthen the life of a hull. More recently, composites have been used for other purposes. For example, some bats are now made from 20 composite materials. For many years, baseball bats and softball bats were made of wood.

Softball bats made of composites have several advantages. Among the advantages is the capability to design and manufacture a bat having consistent performance. Another advantage is that source of composite materials for the manufacture of baseball bats and softball bats is readily available. Baseball bats and softball bats made of natural material, such as ash or very hard pine, are prone to inconsistency and, sadly, the sources of such woods are becoming increasingly scarce. One problem associated with softball bats and baseball bats made of composite materials is the lack of a test for categorizing the performance of various composite softball bats or baseball bats.

Another problem is that it is difficult to determine if a softball bat made of a composite material has been modified to enhance performance. In all 5 walks of life, some individuals seek an unfair advantage. Some softball players and baseball players are no different and will modify a bat to gain an unfair advantage. To date, there does not appear to be a test to determine if a softball bat or baseball bat has been modified. In addition there does not appear to be a testing apparatus that is portable to allow field testing.

A softball or baseball bat formed of composite material also may wear and the performance characteristics may change over time. In the past, there has not been a testing apparatus to monitor these changes.

SUMMARY OF THE INVENTION

A softball bat is made entirely out of composite material. The main portion of the bat includes a substantially tubular hiring surface and a handle. A composite sleeve is added within the hitting surface. The sleeve is made of composite material. The hitting surface is also made of composite material.

Advantageously, the composite material has a lower density than 20 metals used to make bats, such as aluminum or titanium. As a result, more material can be used resulting in a more durable bat for a given weight of bat. The composites also have a higher strength than aluminum and titanium and their alloys. Therefore, a stronger bat can be produced. In addition, the composite does not dent and therefore more energy is transferred to the ball. There is less, if any, energy wasted on denting the bat or the inner sleeve. Therefore, the inventive bat hits farther than a wooden or metal bat or bat having metal parts. The inventive bat is made entirely of composite material. Composite material can be made either stiffer or more flexible than a metal bat. The design parameters of a composite are more flexible so that either a more flexible or stiffer bat can be formed by varying the engineering parameters. The additional flexibility in using composite material allows designers to form bats with selected performance characteristics. If the bat is made to be more flexible, the inventive bat has a durability advantage since the bat does not dent and begin the somewhat slow process of failing.

DESCRIPTION OF THE PREFERRED EMBODIMENT

In the following detailed description of the preferred embodiments, reference is made to the accompanying drawings, which form a part hereof, and in which are shown by way of illustration specific embodiments in which the invention may be practiced. It is to be understood that other embodiments may be utilized and structural changes may be made without departing from the scope of the present invention.

Figures 1, 2:
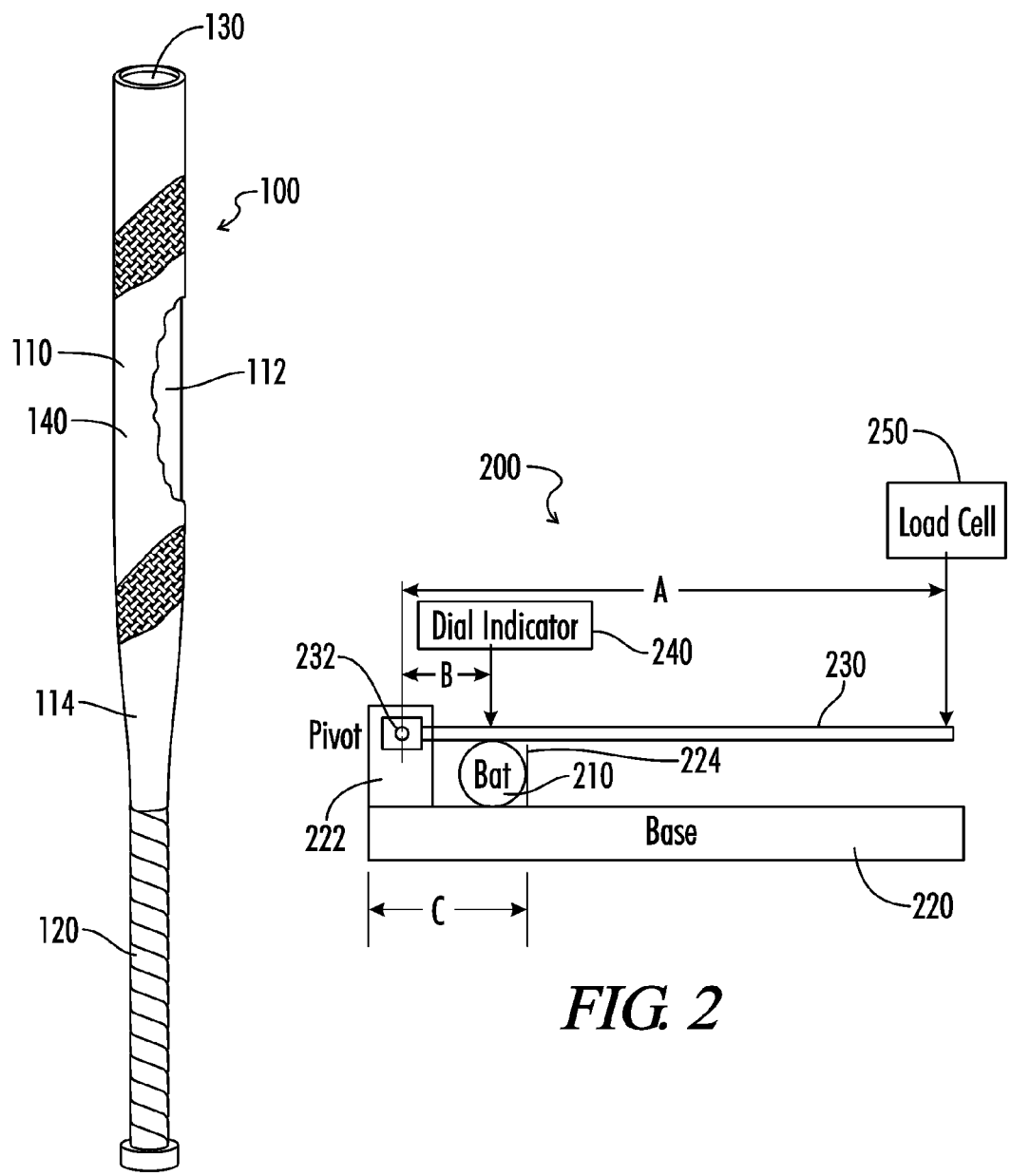
FIG. 1 is a perspective view of a ball bat, with a portion of the tubular hitting surface broken away to show a sleeve according to the present invention.
FIG. 2 is a schematic view of one embodiment of a testing apparatus for measuring the flexibility of a bat.
Figure 3:
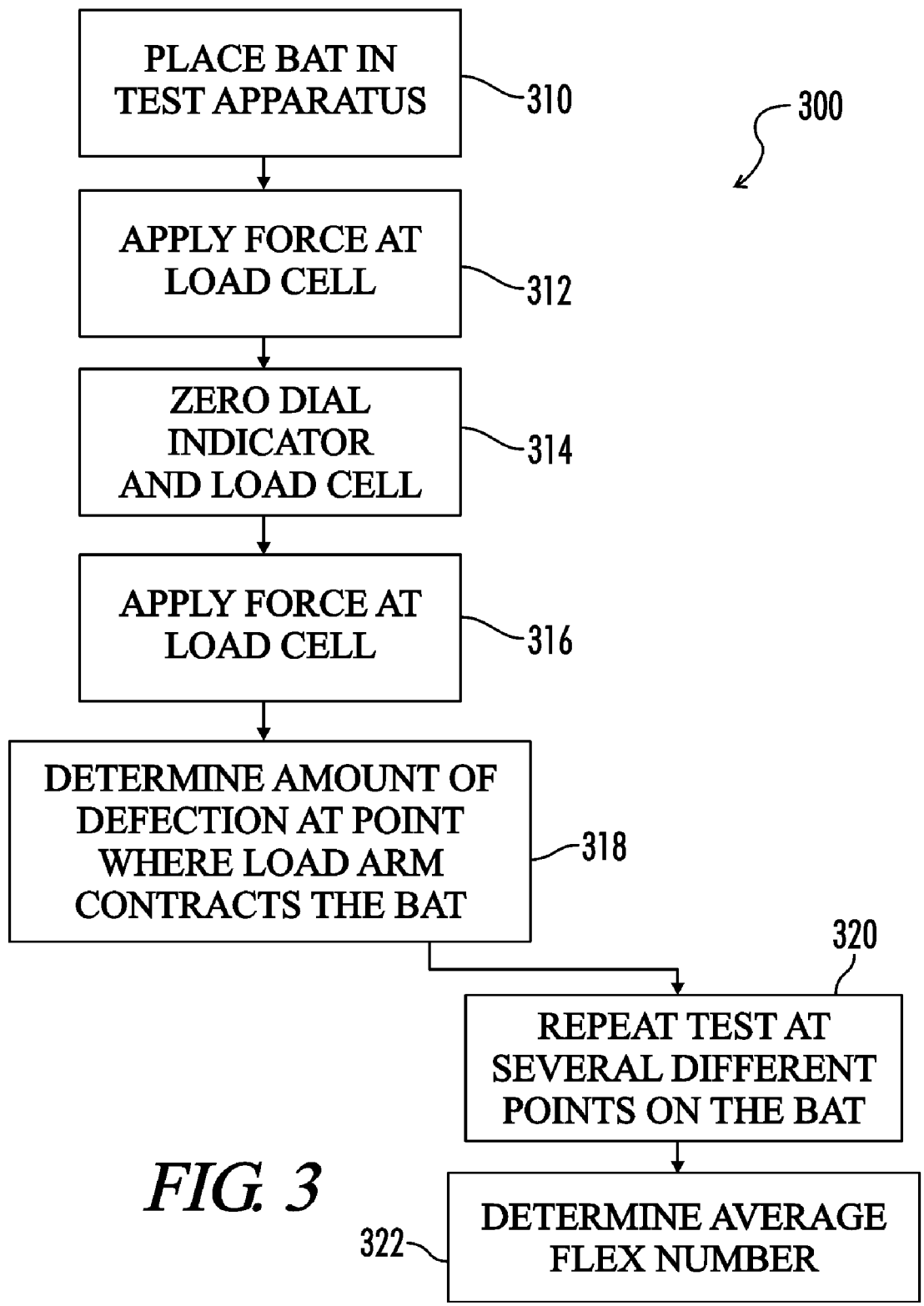
FIG. 3 is flow chart detailing the use of the testing apparatus of the embodiment of the invention shown in FIG. 2.

The invention described in this application is useful with all mechanical configurations of bats including softball bats and baseball bats. FIG. 1 is an exploded view of one type of a bat 100 having a substantially tubular hitting surface 110 and a handle 100. The ball bat 100 is made of composite material. The main portion of the bat 100 includes a substantially tubular hitting surface 110. A handle 120 is attached to the hitting surface. The handle 120 and barrel are integral in the bat shown in FIG. 1. It should be noted that the bat could be formed of a separate handle 120 and tubular hitting surface or barrel 110. The tubular hitting surface 110 and the attached handle 120 form the body 140 of the bat. The diameter of the handle 120 is less than the diameter of the tubular hitting surface 110 and therefore the body 140 of the bat includes a tapered portion 114 that is positioned between the handle 120 and the tubular hitting surface 110. The bat may include a 10 sleeve 112 is within the body 140 of the bat and more specifically within the tubular hitting surface 110. As mentioned above, the ball bat 100 includes one or more portions made a composite material that includes a fiber and a resin. The fibers can be made of Kevlar, graphite, carbon, boron, rayon, nylon, fiberglass, other plastics or other polymer materials. Graphite nano tubes may also be used. The resin or binding material may include thermosetting resin systems, epoxies, ceramics, or thermoplastics. The fibers are impregnated with a resin to form a composite material. A plug 130 is at a free end of the hitting surface 110.

The amount flexibility of a bat is linked to characteristics of favorable bat performance. It should be noted that some favorable performance 20 characteristics may come at the expense of other favorable performance characteristics. In short, there may be a trade off in terms of performance characteristics. An example of this is that the life of a softball bat is generally shortened as the flexibility of the bat increases. In other words, a more flexible, long-hitting softball bat will typically have a shorter useful life than a less flexible, shorter-hitting softball bat.

FIG. 2 is a schematic view of one embodiment of a testing apparatus 200 for measuring the flexibility of a bat 210. The testing apparatus 200 includes a base 220 that includes an upright 222 attached to the base and a datum 224 also attached to the base 220. The datum 224 is spaced away from the upright 222.

Attached to the upright 222 is a load arm 230. The upright 222 has an opening 223 therein. The load arm 230 is attached to the upright by a pivot pin 232. The pivot pin 232 allows the attached end of the load arm 232 to pivot about the opening 223 in the upright 222. A dial indicator 240 is positioned between the upright 222 and the datum 224 and near the load arm 230. The dial indicator 240 is placed so that when the bat 210 is placed in the testing apparatus 200, the dial indicator 240 contacts the bat 210 near the load arm 230. Positioned at or near the free end of the load arm 230 is a load cell 250. The load cell 250 produces a specified load on the free end of the load arm 230. The distance between the pivot point at the center of the pivot pin 232 and the point on the load arm 230 where the load cell 250 acts is designated as dimension "A". The distance between the pivot point at the center of the pivot pin 232 and the point where the load arm 230 contacts the bat 210 is designated as dimension "B". The distance between the end of the base 220 nearest the uptight 222 and the datum 224 is designated as dimension "C". Of course, different embodiments of the testing apparatus 200 have different dimensions (A, B, C). In the embodiment shown in FIG. 2, the dimensions are as follows:

1. A=17 9/16 inches
2. B=2 3/4 inches
3. C=4 inches

Using the testing apparatus 200 described in the example above, bats having a flexibility value above 600 have favorable performance characteristics. Bats having a flexibility in the range of 550 to 1250 units also have favorable performance characteristics.

In operation, the testing apparatus 200 is used to test a bat, such as bat 210, for flexibility. Testing the bat requires a test procedure 300. The test procedure 300 includes placing the bat in the testing apparatus, as depicted by reference numeral 310. The bat 210 is placed on the base 220 and in contact with datum 224. Next, the load cell 250 applies 10 pounds of force at load end or free end of the load arm 230, as depicted by reference numeral 312. The dial indicator 240 and the load cell 250 are each zeroed, as depicted by reference numeral 314. Next, the load cell 250 applies 60 pounds of force at load end or free end of the load arm 230, as depicted by reference numeral 316. The dial indicator 240 is then read to determine the amount of deflection of the bat at the point or in the area where the load arm 230 contacts the bat 210, as depicted by reference numeral 318. This procedure is repeated a number of times around the circumference of the bat 210, as depicted by reference numeral 320. The average value is then used to determine a number to indicate the flexibility of the bat 210, as depicted by reference numeral 322. A flex number for each test may be determined. A fixed load may be placed on the softball bat and the average deflection may also be used to determine a flex number.

One example of a calculation of such a flex number includes dividing the load placed on the arm by the load cell 250 by the amount of deflection indicated by the dial indicator 240. In this example, the load of 60 lbs is divided by the deflection in inches (60 lbs./0.0575"=1043 lbs./inch or 1043 Flex) to yield a flex indication number of 1043. It is contemplated that the flex indication number could be recalibrated thereby producing a new scale. For example, the actual load at the point where the lever arm contacts the softball bat can be used to determine the lbs./inch of flex in the bat. It is further contemplated that other testers or testing 20 apparatus could be used to determine flexibility of the bat 210 under test without departing from the spirit of this invention.

Figure 4:
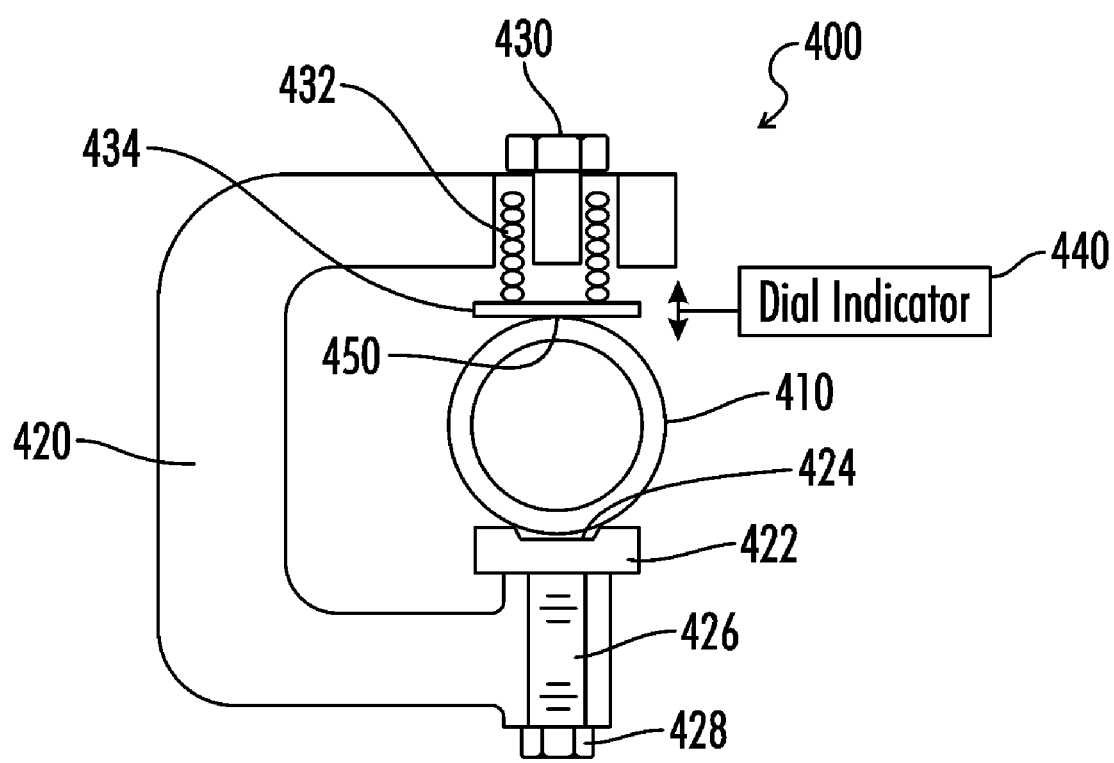
FIG. 4 is a schematic view of another testing apparatus for measuring the flexibility of a bat, according to another embodiment of this invention.

FIG. 4 is a schematic view of another embodiment of a testing apparatus 400 for measuring the flexibility of a bat 210.

A testing apparatus 400 includes a C-shaped element 420. The C-shaped element 420 includes two arms having ends that hold a first fastener 426 and a second fastener 430. The first fastener 426 threads into one end of the C-shaped element 420. The fastener 426 includes a first end 428 which includes an upset end and a second end which includes a base 422. The base 422 includes a depression or feature 424 used to hold a bat 410. Specifically, the feature or depression 424 is shaped to hold the barrel of a bat 410. The base 422 is attached to the first fastener 426. The fastener 426 is used to move the plate 422 into engagement with the bat 410 by turning the fastener 426 and specifically the head of the fastener 428. In this particular embodiment, the head of the fastener 428 is turned until it is finger tight which assures that the bat 410 is engaged with the base 422 and specifically with the depression or feature 424 within the base 422. The other end of the C-shaped member 420 carries fastener 430. Fastener 430 is threadably engaged with the other end of the C-shaped member 420. A spring 432 having a specified force constant is also engaged with the other end of the C-shaped unit 420. The spring is attached to a load beam 434. While the spring is compressed or when the spring is fully compressed, a fixed load is placed on the bat 410 at a point or an edge depicted by reference numeral 450. It should be noted that the load beam 434, as shown in this embodiment, is essentially a flat plate which is used to contact or load the bat or side of the bat 410. It is further contemplated that other geometric shapes could be added to the load beam such as a point or other geometric shape. A dial indicator 440 is attached to the load beam 434. The fastener 430 is tightened until the spring is moved through a specified distance thereby loading the load beam 434 to a specific or specified amount of force. The force can be determined by knowing the force constant of the spring and turning the fastener 430 to compress the spring a 20 selected amount, thereby producing the selected force. The dial indicator 440 indicates the amount of displacement on the surface of the bat 410 or displacement of the bat for the specified load.

It should be noted that in other embodiments of this invention, a different arrangement can be used. For example, it may be advantageous to place a shock load on the bat 410. Therefore, the spring 432 would initially be loaded and suddenly released, thereby forcing the load beam 434 into contact momentarily with the bat 410. The force would be an impulse force or a shock load that would replicate the forces placed on a bat when a ball is hit with the bat 410. The dial indicator 440 can be used to measure the amount of deflection in either the steady application of force embodiment discussed above or for the embodiment where the bat 410 is shock loaded to replicate a hit on a ball with the bat 410.

Figure 5:
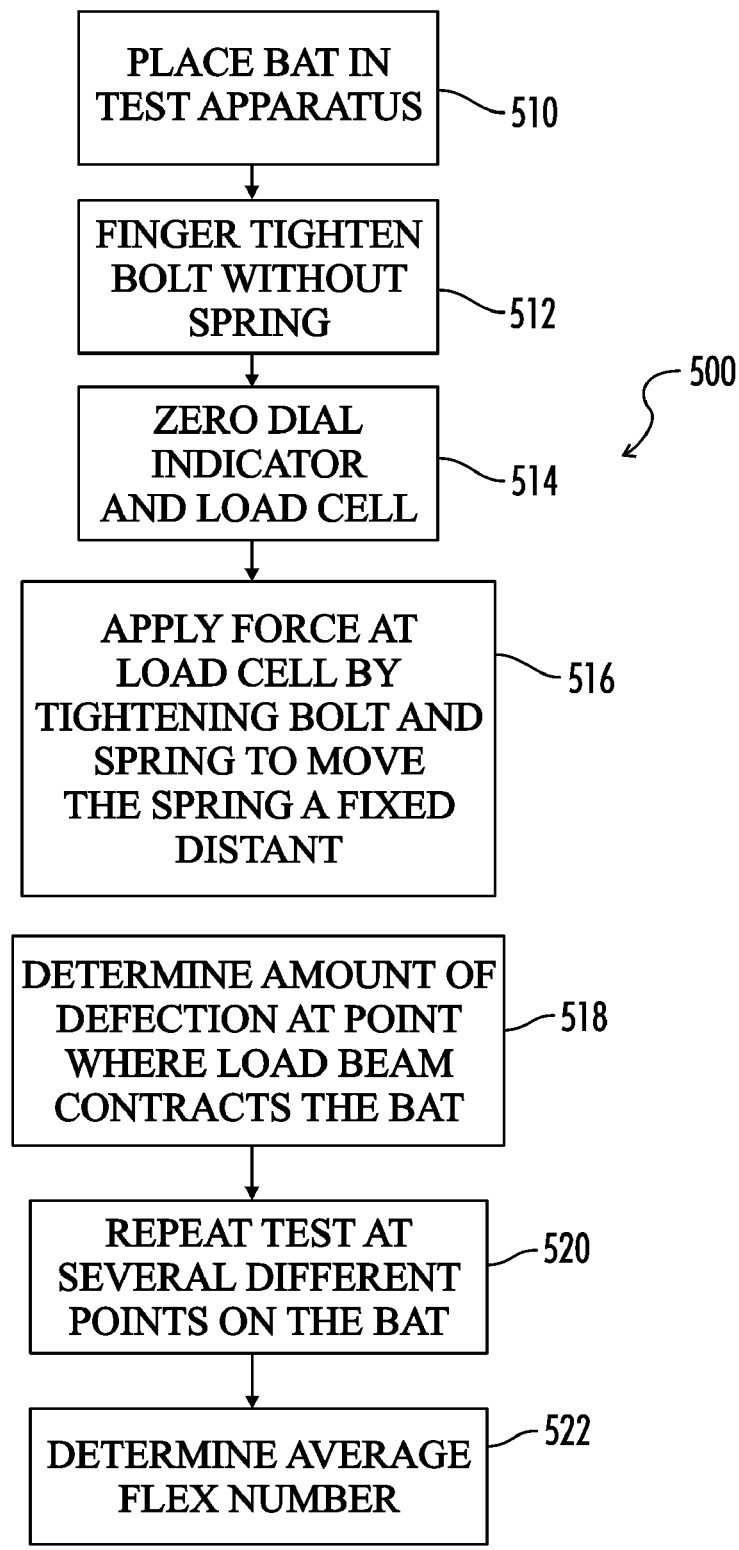
FIG. 5 is an exploded perspective view of a set of sheets pre-impregnated fibers and a mandrel used to form the inner sleeve of the present invention.

Now turning to FIG. 5, a test process 500 will be discussed. Test process 500 includes placing the bat in the test apparatus, as depicted by reference numeral 510. Specifically, the bat 410 is placed in the depression 424 of tire base 422. Next, the first fastener 426 is finger tightened, as depicted by reference numeral 512. The dial indicator 440 is zeroed as is the load ceil, as depicted by reference numeral 514. A force is then applied at point 450 by tightening the second fastener 430 and causing the spring 432 to move through a fixed distance. This causes the spring 432 to place a fixed force on the bat through the load beam 434, as depicted by reference numeral 516. Next, the amount of deflection at the point 450 where the load beam contacts the bat is determined by reading the dial indicator 440, as depicted by reference numeral 518. Once this is completed, a flexibility number, in terms of the pounds per inch of deflection, can then be determined. The test is then repeated at several different points along the bat, as depicted by reference numeral 520. In a preferred embodiment, the test is conducted at several points along the barrel of the bat. The various flex numbers are then averaged or added up to determine an overall flex number.

Advantageously, either of the embodiments of the testing apparatus 200, 400 are portable so that an umpire or a testing organization could test composite articles such as bats 210, 410 in the field. It is contemplated that the flex numbers associated with a particular bat could be placed upon the bat or a directory including all the flex numbers for various softball bats could be placed in either a database or a book form. Softball bats or other composite articles could then be tested in the field to determine if the flexibility number associated with the bat is within an acceptable range of the flexibility number associated with the bat at manufacture. Another formulation of the test might be to set a threshold for flexibility and a threshold number or flexibility number in pounds per inch of deflection over which a bat would no longer qualify or be certified by a certification organization. In this manner, the testing could be random or could be carried out at the request of any person on the field to determine if a particular bat or composite article is within specifications and can be used in a tournament. In this manner, composite articles such as softball bats that have been modified and are now outside the specification of the certification organization can be found in the field. Furthermore, bats or composite articles that have been used and are no longer within spec can also be found in the field. In particularly important games or in particularly important circumstances, all composite articles such as softball bats can be tested prior to the beginning of a contest.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A testing apparatus for a composite bat comprising:
    a base for holding the composite bat;
    a load cell for placing a non-denting static load on a hitting surface of the composite bat; and
    a displacement measuring device operatively attached to the load cell and the base for measuring the amount of radial displacement for the static load on the hitting surface.

2. The testing apparatus for a composite bat of claim 1 wherein base includes a feature for holding a portion of the bat.

3. The testing apparatus for a composite bat of claim 1 further comprising:
    a pivot attached to the base;
    an arm having an attached end and a free end, the attached end of the arm pivotally attached to the pivot, wherein the load cell places a load on a load end of the arm.

4. The testing apparatus for a composite bat of claim 3 wherein the load cell acts on a portion of the arm near the free end of the arm.

5. The testing apparatus for a composite bat of claim 3 wherein the load cell places the load on the arm at a selected location on the arm.

6. The testing apparatus for a composite bat of claim 3 wherein the load cell places the load on the arm at a first selected location on the arm and wherein the composite bat is placed at a second selected location with respect to the arm, wherein the first selected location differs from the second selected location.

7. The testing apparatus for a composite bat of claim 3 wherein the load cell places the load on the arm at a first selected location on the arm and wherein the composite bat is placed at a second selected location with respect to the arm, wherein the first selected location is at a first distance from the pivot point and the second selected location is at a second distance from the pivot point.

8. The testing apparatus for a composite bat of claim 7 wherein the first distance is closer to the pivot point and than the second distance.

9. The testing apparatus for a composite bat of claim 2 further comprising:
    a pivot attached to the base; and
    an arm having an attached end and a free end, the attached end of the arm pivotally attached to the pivot, wherein the load cell places a load on another portion of the arm.

10. The testing apparatus for a composite bat of claim 9 wherein the feature locates a portion of the bat at a first distance from the pivot and wherein the load cell places the load on the arm at a second distance from the pivot.

11. The testing apparatus for a composite bat of claim 10 wherein the second distance from the pivot is greater than the first distance from the pivot.

12. The testing apparatus for a composite bat of claim 9 wherein the second distance where the load cell acts on the arm is a substantially fixed distance from the pivot.

13. A method of testing a composite bat having a hitting area, the method comprising:
    applying a static load to the hitting area on the composite bat;
    measuring the radial displacement of the composite bat; and
    wherein applying a static load on the composite bat includes loading the composite bat within the elastic limit of the composite bat.

14. The method of claim 13 wherein applying a static load on the composite bat includes loading the composite bat without denting the hitting area of the composite bat.

15. The method of claim 13 further comprising dividing the static load placed on the bat by the measured displacement to yield a number representing flexibility of the composite bat.

16. The method of claim 13 wherein applying a static load to a portion of the bat includes placing a load on a plurality of areas associated with a hitting surface of the bat.

17. The method of claim 16 wherein measuring the amount of displacement includes measuring the amount of displacement at the plurality of areas associated with the hitting surface of the bat.

18. A method of testing a bat comprising:
applying a known static load to a point on an area of the bat by loading the bat within the elastic limit of the bat;
measuring the radially displacement of the bat at the point; and
numerically determining the flexibility of the bat by dividing the load placed on the bat by the measured displacement.

* * * * *